US012667205B2

(12) United States Patent　　　　　(10) Patent No.:　US 12,667,205 B2
Crescini et al.　　　　　　　　　　　　(45) Date of Patent:　Jun. 30, 2026

(54) APPARATUS FOR SOOTHING A BABY

(71) Applicant: 2B S.R.L., Rome (IT)

(72) Inventors: Matteo Crescini, Giussano (IT); Luca Sironi, Paina di Giussano (IT); Sveva Belviso, Rome (IT); Michele Guarino, Rome (IT)

(73) Assignee: 2B S.R.L., Rome (IT)

( * ) Notice: Subject to any disclaimer, the term of this patent is extended or adjusted under 35 U.S.C. 154(b) by 1006 days.

(21) Appl. No.: 17/759,642

(22) PCT Filed: Dec. 10, 2020

(86) PCT No.: PCT/IB2020/061753
§ 371 (c)(1),
(2) Date: Jul. 28, 2022

(87) PCT Pub. No.: WO2021/152385
PCT Pub. Date: Aug. 5, 2021

(65) Prior Publication Data
US 2023/0099651 A1　　Mar. 30, 2023
US 2024/0008660 A2　　Jan. 11, 2024

(30) Foreign Application Priority Data

Jan. 29, 2020　(IT) ........................ 102020000001714

(51) Int. Cl.
*A47D 15/00*　　　(2006.01)
*A61M 21/02*　　　(2006.01)
*A61M 21/00*　　　(2006.01)
(52) U.S. Cl.
CPC ........... *A47D 15/001* (2013.01); *A61M 21/02* (2013.01); *A61M 2021/0022* (2013.01);
(Continued)

(58) Field of Classification Search
CPC ............................................... A61M 21/00–02
See application file for complete search history.

(56) References Cited

U.S. PATENT DOCUMENTS 10,238,341 B2　3/2019　Rubin et al.
2015/0038072 A1　2/2015　Cordier et al.
(Continued)

FOREIGN PATENT DOCUMENTS

KR　　20120000342 U　　1/2012
KR　　　101798498 B1　　11/2017
(Continued)

OTHER PUBLICATIONS

International Search Report and Written Opinion for International Patent Application No. PCT/IB2020/061753, mailed Feb. 16, 2021, 9 pages.
(Continued)

*Primary Examiner* — Thaddeus B Cox
(74) *Attorney, Agent, or Firm* — Armstrong Teasdale LLP

(57) ABSTRACT

An apparatus for soothing a baby on a mattress has a mattress support or base having weight detecting means for detecting weight of the baby on the mattress, cry detecting means for detecting baby cry, and vibration means for vibrating the mattress. The apparatus has control means configured to determine a center of gravity of the baby on the mattress and baby agitation in response to the weight detecting means. The control means control the vibration means to vibrate the mattress in a position different from the center of gravity of the baby on the mattress within and not beyond a maximum time in response to detection of the baby's cry and/or agitation.

12 Claims, 4 Drawing Sheets

(52) U.S. Cl.
CPC ................. *A61M 2205/332* (2013.01); *A61M*
*2205/3375* (2013.01); *A61M 2205/50*
(2013.01)

(56) References Cited

U.S. PATENT DOCUMENTS

2016/0022525 A1* 1/2016 Galitzer ................. A61H 1/001
128/845
2017/0169690 A1* 6/2017 Pfeiffer ............... B60N 2/0029

FOREIGN PATENT DOCUMENTS

WO      2013059625 A1    4/2013
WO      2018075566 A1    4/2018

OTHER PUBLICATIONS

N. Zhang et al., The effects of physical vibration on heart rate variability as a measure of drowsiness, Ergonomics, published online Jul. 17, 2018, pp. 1259-1272, vol. 61, Issue 9, Taylor & Francis Group, GB.

* cited by examiner

APPARATUS FOR SOOTHING A BABY

CROSS-REFERENCE TO RELATED APPLICATION

This application is a National Stage Application of International Patent Application No. PCT/IB2020/061753, having an International Filing Date of Dec. 10, 2020, which claims priority to Italian Application No. 102020000001714, filed Jan. 29, 2020, each of which is hereby incorporated by reference in its entirety.

FIELD OF THE INVENTION

The present invention relates to an apparatus for soothing a baby.

BACKGROUND ART

It is known in the background art that vibrations at a determined frequency can conciliate sleep. In particular, a recent study published in the journal Ergonomics by N. Zhang, M.Fard, M H U Bhuiyan, D. Verhagen, M F Azari and S. R. Robinson, entitled: "The effects of physical vibration on heart rate variability as a measure of drowsiness", discloses how scholars have found that constant vibrations at low frequencies (for example, those we experience when we are in a car) lull the brain and body and, when this occurs, the sensory input coming from the vibrations begins to synchronize the brain waves and "make the brain sleep". In particular, this frequency is very close to that of "theta waves", i.e., a type of brain waves connected with the entry into the state of sleep, which generate the "theta rhythm", a neural oscillatory pattern which can be detected in the performance of an electroencephalogram (EEG).

Although two types of theta rhythms have been described, a "hippocampal theta rhythm" (which exhibits a strong oscillation) and a "cortical theta rhythm" (which represents the low frequency component of the EEG), in general, the term theta refers to frequency components in the range between 4 and 7 Hz, regardless of the source thereof. Cortical theta is frequently observed in young children, while in older children and adults it tends to appear during meditative, somnolent, hypnotic, or dormant states, and not during the deeper stages of sleep. Consequently, since in the literature EEGs show that when subjects fall asleep, theta wave activity increases.

The vibrations are "mechanical oscillations generated by pressure waves which are transmitted through elastic solid bodies, around a reference position"; if these occur with a frequency greater than 15-20 "repetitions per second" (abbreviated in "Hertz"), the vibration is acoustic, i.e., it produces an audible sound. If, on the other hand, the cadence is lower, the vibration can be called mechanical or vibration proper. The vibrations are divided into 3 main frequency bands and low frequency oscillations are generated by transport means (land, air, sea). In addition to frequency, the vibrations are characterized by three other parameters which are closely related to each other amplitude, i.e., the maximum movement from the equilibrium position;

speed with which the movement occurs;

acceleration, i.e., speed variation.

Of these parameters, acceleration is the most important for evaluating the body's response to vibrations, as humans feel the variation of a stimulus more than the persistence thereof.

WO2018075566A1 and WO2013059625A1 describe apparatuses adapted to analyze a baby's cry and adapted to intervene by activating the vibration of a mattress on which the baby lies only when the audio signal indicative of the baby's cry exceeds a certain threshold.

U.S. Pat. No. 10,238,341B2 describes an apparatus capable of processing a baby's cry, determining the Fourier transform and the standard deviation of the Fourier transform. The baby's state is determined based on this standard deviation, for example by comparing it with values entered in one or more data tables to verify if the standard deviation value corresponds to one of the sound values generated by a baby. Action is taken, such as adjusting the vibration intensity, based on the baby's state.

In view of the background art, it is the object of the present invention to provide an apparatus for soothing a baby which is different from those which are known.

SUMMARY OF THE INVENTION

In accordance with the present invention, such an object is achieved by means of an apparatus for soothing a baby arranged in a mattress, said apparatus comprising a mattress support or base comprising:

means for detecting the baby's weight on the mattress, means for detecting the baby's cry, means for vibrating the mattress, characterized in that it comprises control means adapted to determine the baby's center of gravity on the mattress and to determine the baby's agitation in response to said weight detecting means of the baby on the mattress, said control means being adapted to control said mattress vibration means in a position different from the baby's center of gravity on the mattress and within and not beyond a maximum time period in response at least to the detection of the baby's cry and/or agitation.

DRAWINGS

The features and advantages of the present invention will become apparent from the following detailed description of a practical embodiment thereof, shown by way of non-limiting example in the accompanying drawings, in which.

Figure 1:
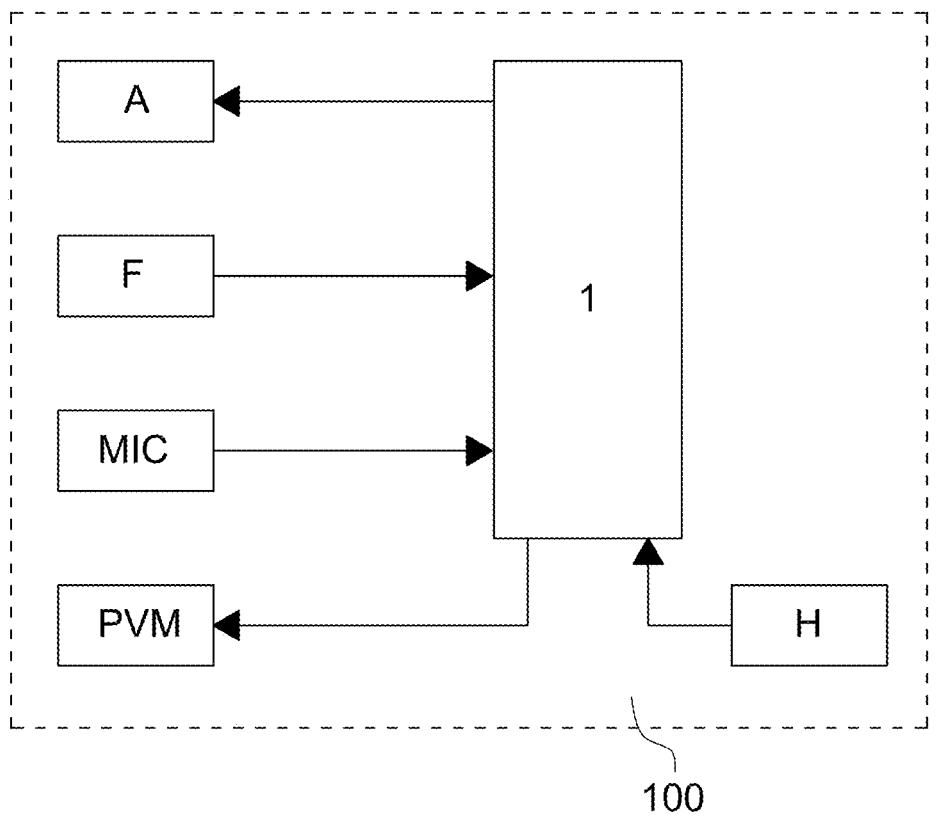
FIG. 1 shows an apparatus for soothing a baby in accordance with the present invention.
Figure 2:
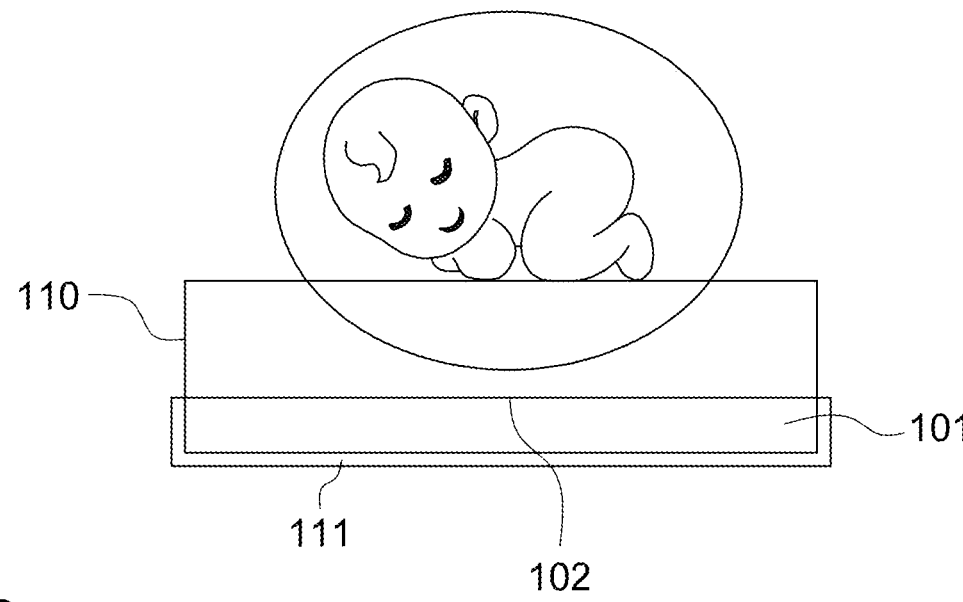
FIG. 2 shows a mattress comprising the apparatus of FIG. 1.
Figure 3:
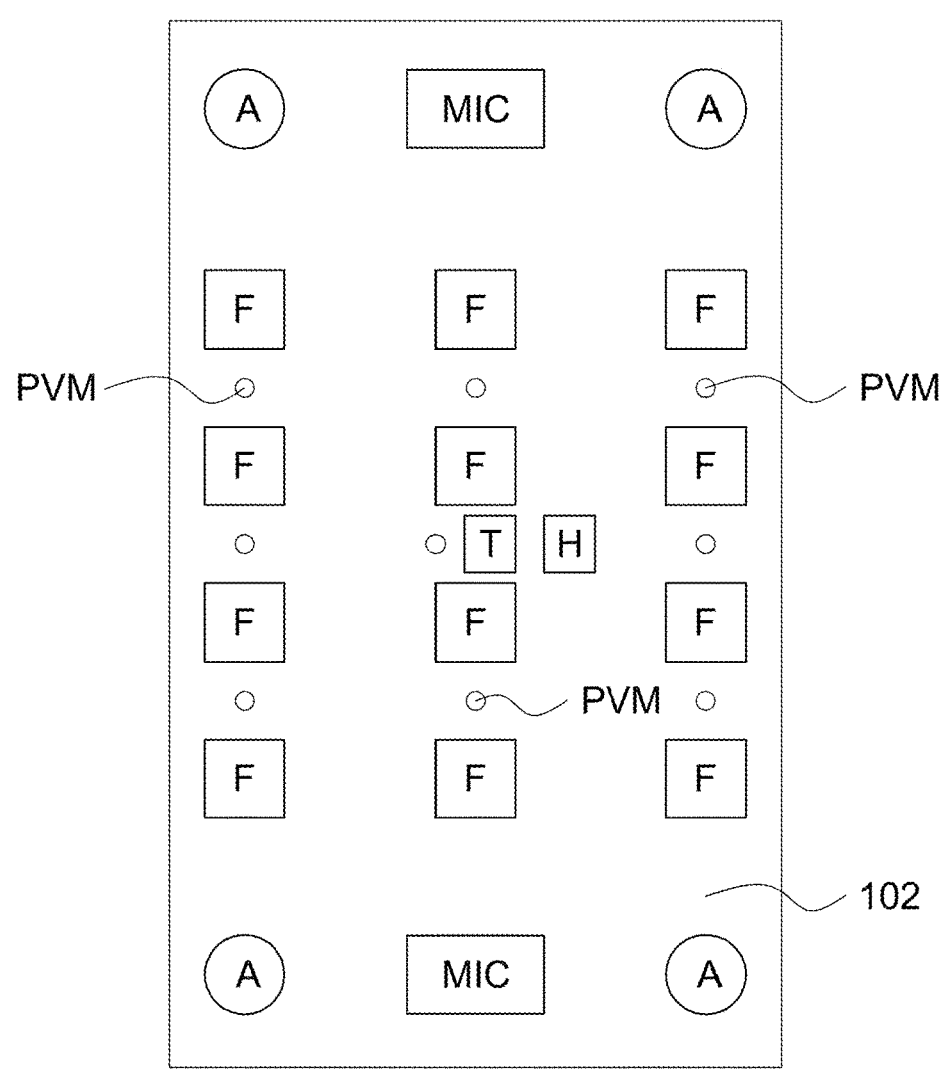
Figure 4:
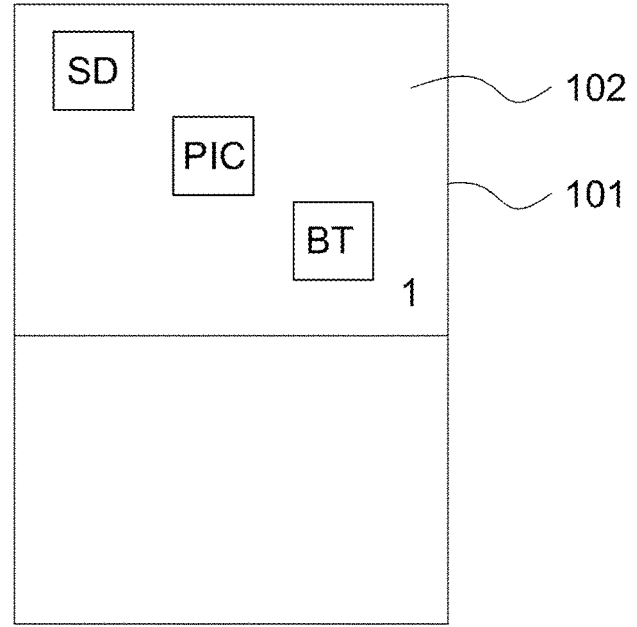
Figure 5:
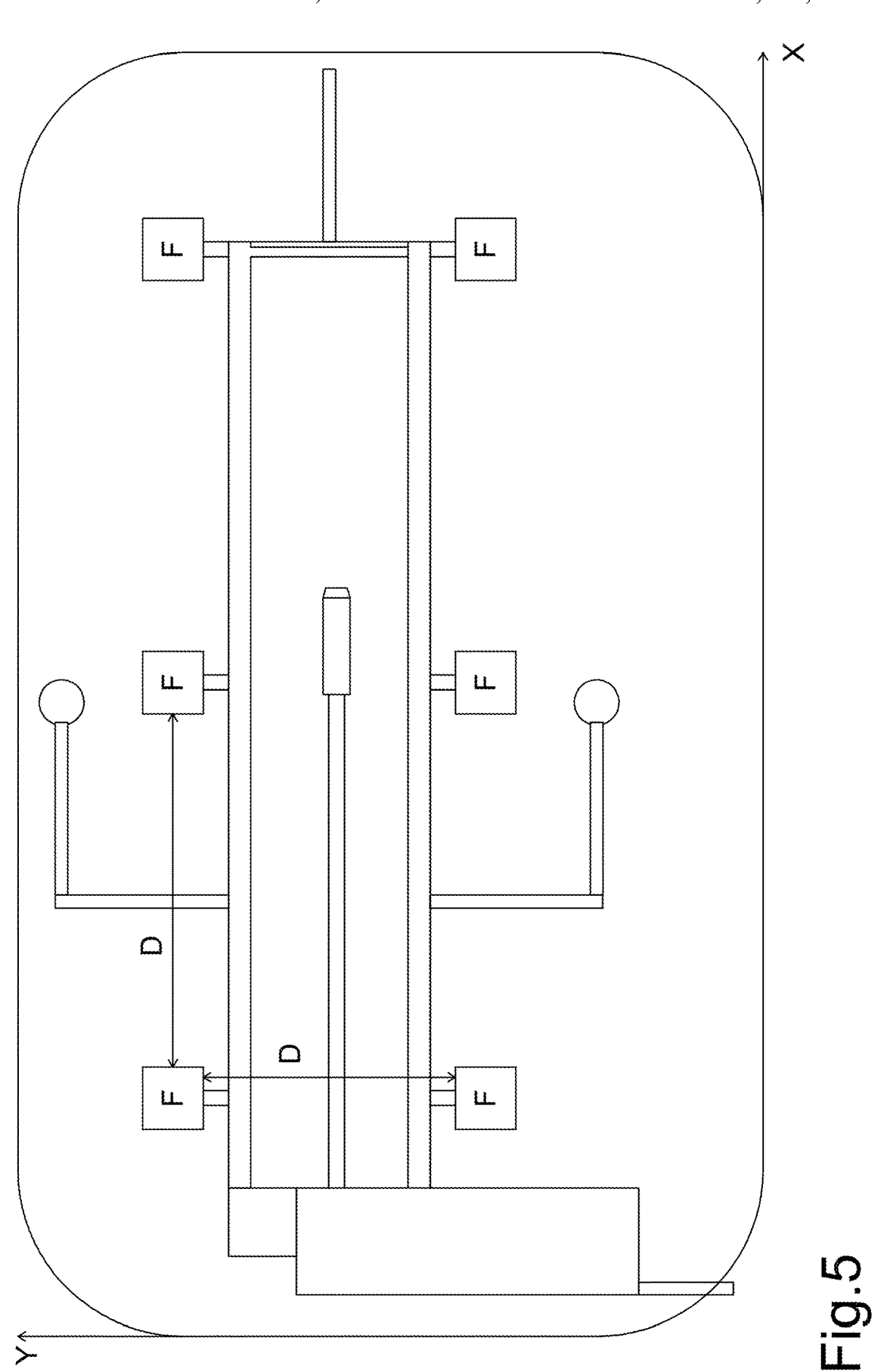
Figure 6:
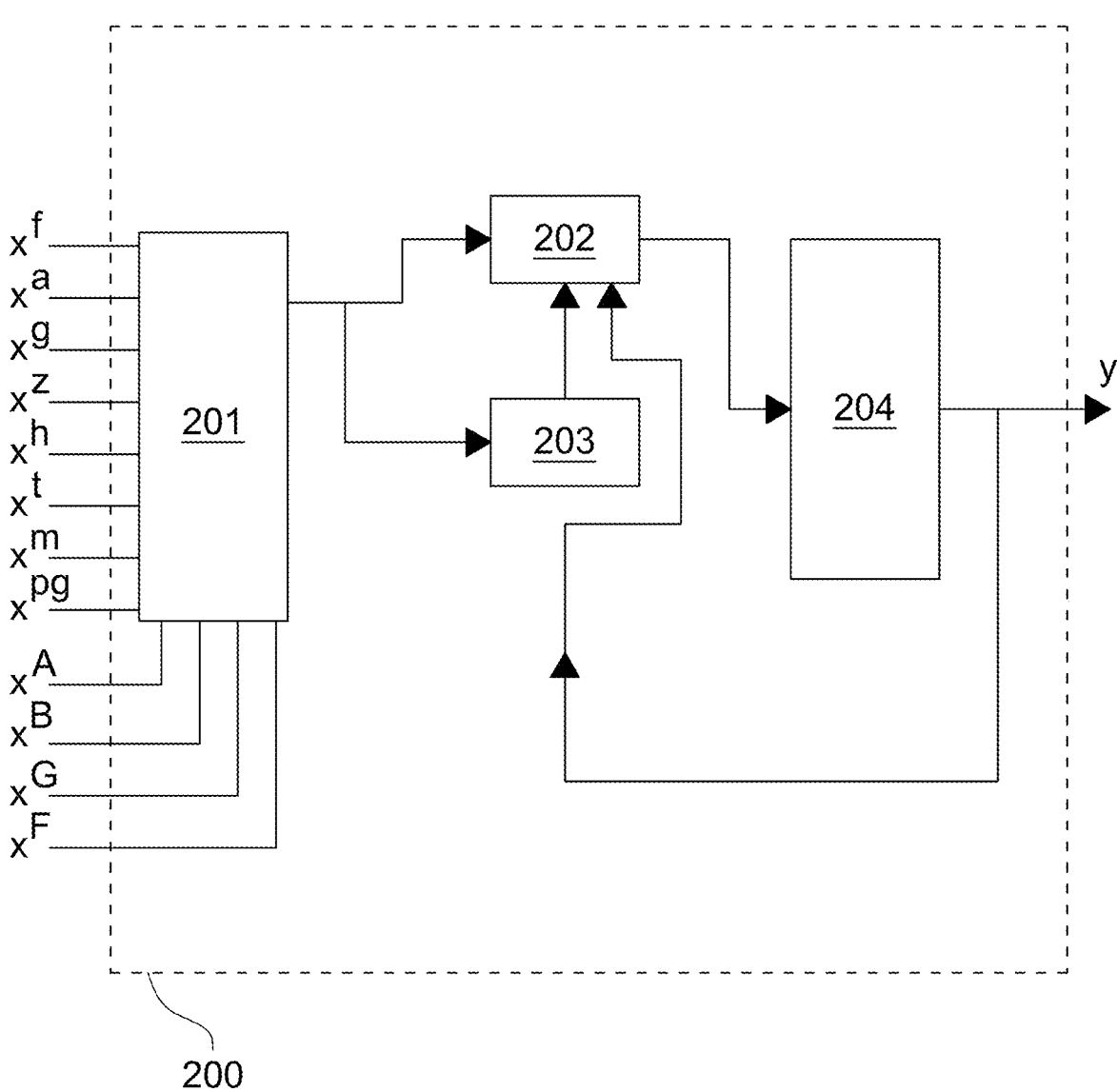

FIGS. 3 and 4 schematically show the apparatus in accordance with the present invention arranged in the mattress base of FIG. 2;

FIG. 5 shows an embodiment of the apparatus in accordance with the invention on the mattress base;

FIG. 6 shows the fuzzy logic of the control unit of the apparatus of FIG. 1.

DESCRIPTION OF SOME PREFERRED EMBODIMENTS

FIGS. 1-6 describe an apparatus 100 for soothing a baby, in particular a baby from 0 to 36 months, in accordance with the present invention.

The apparatus 100, seen in FIG. 1, comprises an electronic control unit 1 which is electrically connected to a plurality of microphones MIC, to a plurality of temperature sensors T, to a plurality of speakers A, to a plurality of force sensors F and to a plurality of vibration generating means PVM, for example piezoelectric means, and a humidity sensor H.

Preferably, the apparatus 100 is arranged on a base 101 of the baby's bed (FIGS. 2-5), preferably a wooden and preferably rectangular base, above the upper face 102 of which a mattress 110 is arranged on which the baby is placed for sleep. A padding 111 of the base 101 is preferably provided to protect the electronic devices installed in the base.

As seen in FIG. 3, in the upper part 102 of the base 101 two microphones MIC are arranged adjacent to the short sides of the base 101, two speakers A, a temperature sensor T, a plurality of force sensors F and a plurality of vibration means PVM.

As seen in FIG. 4, the upper part 102 of the base 101 comprises the control unit 1 comprising an electronic board in which the microprocessor PIC is mounted, a removable memory card SD and preferably a module BT of radiofrequency data transmission/reception RF preferably of the wireless type, preferably compatible with the transmission/reception of data through the Bluetooth protocol. The power supply of the apparatus 100 is external, preferably by means of a battery. The base 101 has tracks for the electrical connection of the devices present on the upper part 102 with the unit 1. Alternatively, the control unit 1 is outside the base 101; the base always comprises a control unit which communicates wirelessly with the control unit 1 through the module RF.

The speakers A allow the broadcast of music or a message from the baby's mother which is contained in the memory SD of the unit 1.

The temperature sensor T is adapted to detect the temperature inside the baby's bed and send it to the unit 1 for the comparison with predefined temperature thresholds.

The sensors of the plurality of force sensors F are arranged according to an $a \times b$ matrix which allows to identify the baby's position on the mattress, i.e., the center of gravity Spar thereof and calculate the baby's weight. The force sensors are arranged at a certain distance D therebetween and at a distance Da from the sides of the mattress, for example the distance D=17.5 cm and the distance Da is 15 cm for a mattress of length 80 cm and width 47.5 cm, as seen in FIG. 5.

Preferably, the vibration means PVM are also arranged in accordance with a matrix.

The electronic board is also provided with a capacitor C which detects the intensity of the baby's cry; the capacitor C is powered by the electrical signal produced by the microphones MIC used to detect the baby's cry.

The control unit 1 is also adapted to detect the fundamental frequency of the baby's cry through the data detected by the microphones MIC and processed by the unit 1.

The control unit 1 is also adapted to detect the humidity of the mattress through the data detected by the humidity sensor H.

The apparatus 100 is adapted to control the vibration of the actuators PVM to induce vibrations of the mattress and to soothe the baby.

The control unit 1 preferably comprises an executive software FL which operates according to a fuzzy logic implementing a fuzzy logic controller 200 shown in FIG. 6. The controller 200 comprises a fuzzification interface or fuzzifier 201 which distinctly transforms the measured data into suitable linguistic values, following a fuzzification procedure which transforms objective data into subjective data through a mapping of the inputs into labels of fuzzy sets in each specific reference universe, converting each input value $x_i$ into a single input value pair and membership function $(x_i, \mu_i(x))$ and for this the whole set is understood as the union of the single components thereof. The base fuzzy control rules are characterized by a collection of fuzzy IF→THEN rules in which the preconditions (antecedents) and consequents involve variables, according to this form:

$R^i$: IF x is $A_i$, . . . , AND y is $B_i$, THEN z is $C_i$ i=1 . . . n.

where x, . . . , y and z are variables representing the process state variable and the control variable respectively and $A_i$, . . . , $B_i$, are the values of the variables x, . . . y and z.

The controller 200 comprises the inference motor 202 and a database comprises the base rules 203. The inference motor must calculate the membership functions and must process the system output as a function of the variables input by the fuzzifier 201 and as a function of the base rules 203. Furthermore, the controller 200 is of the closed-loop type since the membership functions are also calculated as a function of the results of the previous cases.

Preferably, the data processing also occurs in a dedicated partition of a webserver, where the base rules and the inference motor integrated in each apparatus 100 are replicated and reside locally. In this case, the system behaves like an indirect monitoring apparatus of the baby's state and the use of the controller 200 allows to manage this task and to characterize the type of crying; this occurs following a continuous acquisition process of the inputs and processing of the output, for all the apparatuses 100 connected to the network. Consequently, all the apparatuses 100 connected to the network can draw on these resources in the fuzzification and defuzzification process, by connecting to the aforementioned webserver, by means of a connection preferably of the HTTPS type. In the connection, each apparatus 100 feeds an existing database with the value updated at the last reading of each parameter which defines the individual rules, which are thus updated continuously and over time, for each apparatus 100 in the network. At the end of each day the average of each parameter is calculated and such a value is made available for download, preferably of the HTTPS type, to each connected apparatus 100 in the network. The aforementioned upload and/or download connection to the WEB-Server is guaranteed by the use of a mobile gateway (to which the apparatus 100 connects wirelessly, Bluetooth compatible). Therefore, when installing each apparatus 100, by connecting to such a WEB Server, this can download the values of the parameters of the updated rules, without starting from the initial value defined by the single rule.

The controller 200 also comprises a defuzzifier 204 adapted to convert the linguistic values output into data, in particular into voltage or current values for the vibration of the mattress.

The apparatus 100 provides that some input data are entered by a parent or the like; these data are the baby's age, weight and sex $x^s$ (male M or female F).

The sampling of the input signals to the controller 200 is performed by the software FL run by the microprocessor PIC with sampling times which vary as a function of the signal in input. The sampling of the audio signal and of the pressure level occurs with a frequency of 1 s while the sampling of the temperature signal and of the humidity signal occurs with a frequency of 30 s.

The center of gravity $s_{bar}$ of the baby's body on the mattress is deduced from the reading value of the force or pressure sensor F positioned in the position (i; j) in the $a \times b$ matrix of the force sensors F. The system detects the pressure level s on the force sensor F, i.e., a voltage variation on the force sensor in the position (i; j) due to a pressure of the baby's body in that position; if such a pressure s is higher than a reference threshold indicated as $s_{max}$ the system detects such a condition as confirmation that the baby is present in that position. The position (i; j) may not be single; in this case the system checks that the two positions are adjacent.

The digital electrical value or signal $x^f$ is acquired in Volts for each force sensor F and said value is converted into grams obtaining the value $s_g$. The value $x^f$ is acquired if the corresponding pressure value s is greater than the reference value $s_{max}$, which is the pressure value, converted into grams, which is read in conditions of the baby's absence from the crib and/or in conditions where no force is applied in that position except the weight of the mattress and/or the material above the force sensor F.

The center of gravity of the pressure on the mattress is given by:

$$S_{bar} = \left\{ x_{bar} = \frac{\sum\limits_{\substack{i=1 \\ j=1}}^{\substack{i=a \\ j=b}} s_g(i;j) * x_{i;j}}{\sum\limits_{\substack{i=1 \\ j=1}}^{\substack{i=a \\ j=b}} s_g(i;j)} ; y_{bar} = \frac{\sum\limits_{\substack{i=1 \\ j=1}}^{\substack{i=a \\ j=b}} s_g(i;j) * y_{i;j}}{\sum\limits_{\substack{i=1 \\ j=1}}^{\substack{i=a \\ j=b}} s_g(i;j)} \right\}$$

where a and b can have values between 1 and n, $x_{i,j}$ is the coordinate on the abscissa axis of the force sensor in the position i;j, $y_{i,j}$ is the coordinate on the ordinate axis of the force sensor in the position i;j. $x_{bar}$ and $y_{bar}$ are the coordinates on the abscissa and ordinate axes of the center of gravity $s_{bar}$. The reference system used, considering a rectangular shape of the mattress, is that seen in FIG. 5, with the x-axis of the abscissa on the long side and the y-axis of the ordinate on the short side.

The audio signal is acquired by the microphones MIC as an analog value. A Fourier transform is applied to this signal to identify the Fundamental Frequency of the audio signal $x^a$. The rule regarding the cry signal is as follows:

IF (200 Hz)$\leq x^a \leq$(500 Hz) THEN THE BABY IS CRYING.

If the baby is crying, the membership function of the audio signal is calculated as a function of the fundamental frequency $x^a$ which is as follows:

$$\mu(x^a) = \exp\left(\frac{(x^a - m^a)^2}{(\sigma^a)^2}\right)$$

Where $m^a$ is the center of the bell-shaped function and is calculated as follows:

If $x^s$=M, i.e., the baby is male, then:

$$m^a = \begin{cases} 370\,\text{Hz}, & \text{as initial value} \\ m^a + 5\,\text{Hz}, & \text{IF } x^z_{t_{max}} \neq 0, \\ m^a - 5\,\text{Hz}, & \text{IF } x^z_{t_{max}} = 0 \end{cases}$$

with $T_{max}$ maximum duration of vibration.

If $x^s$=F, i.e., the baby is female, then:

$$m^a = \begin{cases} 320\,\text{Hz}, & \text{as initial value} \\ m^a + 5\,\text{Hz}, & \text{IF } x^z_{t_{max}} \neq 0, \\ m^a - 5\,\text{Hz}, & \text{IF } x^z_{t_{max}} = 0 \end{cases}$$

$\sigma^a$ is the width of the bell-shaped function, and is calculated as follows:

$$\sigma^a = \begin{cases} 300\,\text{Hz}, & \text{as intial value} \\ \sigma^a + 50\,\text{Hz}, & \text{IF } x^z_{t_{max}} \neq 0, \\ \sigma^a - 50\,\text{Hz}, & \text{IF } x^z_{t_{max}} = 0 \end{cases}$$

where $$x^z_{t_{max}}$$

is the cry intensity at the time $t_{max}$ after a vibration of the mattress has already occurred for the time $t_{max}$.

Consequently, the width and center of the bell change as a function of the cry intensity value at the time $t_{max}$. In particular, the initial value of ma is 320 Hz for females and 370 Hz for males; if at tmax $$x^z_{t_{max}} \neq 0$$

(i.e., the cry intensity is different from zero) it means that the baby has not been soothed and therefore $m^a$ is increased gradually by 5 Hz and $\sigma^a$ by 50 Hz to contribute to a higher vibration intensity at the same frequency of the baby's cry. Conversely, if at $t_{max}$ the cry intensity is equal to zero, it means that the baby has soothed and therefore $m^a$ is decreased by 5 Hz $\sigma^a$ by 50 Hz to contribute to a lower vibration intensity at the same frequency of the baby's cry.

The cry intensity is detected by the energy accumulated across the capacitor C and, after sampling, the related digital signal $x^z$ is obtained.

The fuzzy rule on cry intensity is as follows:

IF $x^z \neq 0$ THEN THE BABY IS CRYING

If the baby cries, the membership function of the cry intensity is calculated, which is as follows:

$$\mu(x^z) = \begin{cases} 1 - (Z\text{max} - x^z)/(Z\text{max} - Z\text{min}), & \text{for } Z\text{min} \leq x^z \leq Z\text{max} \\ 1, & \text{for } x^z > Z\text{max} \\ 0, & \text{for } x^z < Z\text{min} \end{cases}$$

where $$Z\text{max} = \begin{cases} 5V, & \text{initial value} \\ Z\text{max} - 0.10\ \text{V}, & \text{if } x^z_{t_{max}} \neq 0 \\ Z\text{max} + 0.10\ \text{V}, & \text{if } x^z_{t_{max}} = 0 \end{cases}$$

$$Z\text{min} = \begin{cases} 1V, & \text{initial value} \\ Z\text{min} - 0.05\ \text{V}, & \text{if } x^z_{t_{max}} \neq 0 \\ Z\text{min} + 0.05\ \text{V}, & \text{if } x^z_{t_{max}} = 0 \end{cases}$$

If the baby cries, the mattress vibrates in a different position than the baby's center of gravity $s_{bar}$ for a time period which is at most $t_{max}$.

$Z_{min}$ and $Z_{max}$ represent the minimum and maximum value of the baby's cry intensity which vary as a function of the value $$x_{t_{max}}^z,$$

which the value of the cry intensity at time $t_{max}$ of the previous operation carried out by the apparatus 100 when the baby cried or was agitated and after the vibration of the mattress occurred for the time period from O to $t_{max}$. The initial value of $Z_{min}$ is 1V, while the initial value of $Z_{max}$ is 5V. If at $t_{max}$ the cry intensity is different from zero, it means that the baby has not been soothed and therefore $Z_{max}$ is gradually reduced by 0.10 V to contribute to a higher vibration intensity for the same intensity value of the baby's cry. Conversely, if at $t_{max}$ the cry intensity is equal to zero, it means that the baby has soothed and therefore $Z_{max}$ is increased by 0.10 V to contribute to a lower vibration intensity for the same intensity value of the baby's cry. This process is continuous and within the limits of 0-5V of vibration intensity.

Preferably another input of the controller 200 is the digital signal of the baby's agitation $x^g$ which is deduced from the processing of the analog signal $x^f$ which is the value in Volts for each force sensor F. It is weighted by an agitation index $\rho$, which has a value of 0 or 1. If $$x_{k+1}^f \neq x_k^f,$$

where k is the sampling time (1 s), then the agitation index $\rho_i$ is 1, otherwise it is 0.

The baby's agitation is $$x^g = \frac{\sum_{k=1}^{i=axb} \rho_i}{axb}.$$

The rule of the fuzzy check is:
IF $x^g \neq 0$ THEN THE BABY IS AGITATED
If the baby is agitated, the membership function is calculated, which is as follows:

$$\mu(x^g) = \begin{cases} 1 - \dfrac{G_{max} - x^g}{G_{max} - G_{min}}, & \text{for } G_{min} \leq x^9 \leq G_{max} \\ 1, & \text{for } x^g > G_{max} \\ 0, & \text{for } x^g < G_{min} \end{cases}$$

When $$G_{max} = \begin{cases} 1, & \text{initial value} \\ G_{max} - 0.10, & \text{if } x_{t_{max}}^g \neq 0 \\ G_{max} + 0.10, & \text{if } x_{t_{max}}^g = 0 \end{cases}$$

$$G_{min} = \begin{cases} 1, & \text{initial value} \\ G_{min} - 0.10, & \text{if } x_{t_{max}}^g \neq 0 \\ G_{min} + 0.10, & \text{if } x_{t_{max}}^g = 0 \end{cases}$$

$G_{min}$ and $G_{max}$ represent the minimum and maximum values of the baby's agitation, which vary according to the value $$x_{t_{max}}^g,$$

i.e., the agitation intensity at the time $t_{max}$ after the vibration of the mattress for the time $t_{max}$. The initial value of $G_{min}$ is 0, while the initial value of $G_{max}$ is 1. If at $t_{max}$ the agitation intensity is different from zero, it means that the baby has not been soothed and therefore $G_{max}$ is gradually reduced by 0.10 to contribute to a greater vibration intensity for the same agitation value of the baby. Conversely, if at $t_{max}$ the agitation intensity is equal to zero, it means that the baby has soothed and therefore $G_{max}$ is increased by 0.05 to contribute to a lower vibration intensity for the same agitation value of the baby. This process is continuous and within the 0-1 limits of agitation.

Preferably another input of the controller 200 is the digital temperature signal $x^t$ of the mattress where the baby sleeps, which is deduced from the reading value of the temperature sensor T integrated in the mattress. The system digitally detects the temperature value, in ° C. If the temperature value is lower than an indicated reference threshold $T_{min}$ (e.g., 15° C.), it detects such a condition as a confirmation that the temperature is too low. If the temperature value is higher than a reference threshold indicated as $T_{max}$ (e.g., 40° C.), the system detects such a condition as a confirmation that the temperature is too high. The rules are as follows:

IF $x' \leq T_{min}$ THEN THE TEMPERATURE OF THE MATTRESS IS TOO LOW
and therefore $x^{tmin} = 1$.

Knowing that the temperature of the mattress is too low is useful because a mattress which is too cold creates discomfort for the baby and therefore negatively contributes to the soothing thereof.

IF $x' \leq T_{max}$ THEN THE TEMPERATURE OF THE MATTRESS IS TOO HIGH and therefore $x^{tmin} = 1$.

Knowing that the temperature of the mattress is too high is useful because an overly hot mattress creates discomfort for the baby and therefore negatively contributes to the soothing thereof.

If the mattress temperature is too low or too high, the temperature membership function $x^t$ is calculated, which is the following $$\mu(x^t) = \begin{cases} \exp\left(\dfrac{(x^t - m^{t1})^2}{(\sigma^{t1})^2}\right), & x^t < 20° \text{ C.} \\ \exp\left(\dfrac{(x^t - m^{t2})^2}{(\sigma^{t2})^2}\right), & \text{otherwise.} \end{cases}$$

where $m^{t1}$ is the center of the bell-shaped function related to low temperatures and is calculated as follows:

$$m^{t1} = \begin{cases} 17.5° \text{ C.}, & \text{initial value} \\ m^{t1} + 0.1° \text{ C.}, & \text{IF } x_{t_{max}}^z \neq 0 \text{ or } x_{t_{max}}^g \neq 0, \\ m^{t1} - 0.1° \text{ C.}, & \text{IF } x_{t_{max}}^z = 0 \text{ and } x_{t_{max}}^g = 0, \end{cases}$$

$m^{t2}$ is the center of the bell-shaped function related to high temperatures and is calculated as follows:

$$m^{t2} = \begin{cases} 30° \text{ C.,} & \text{initial value} \\ m^{t2} + 0.1° \text{ C.,} & \text{IF } x^z_{t_{max}} \neq 0 \text{ or } x^g_{t_{max}} \neq 0, \\ m^{t2} - 0.1° \text{ C.,} & \text{IF } x^z_{t_{max}} = 0 \text{ and } x^g_{t_{max}} = 0, \end{cases}$$

$\sigma^{t1}$ is the width of the bell-shaped function related to low temperatures and is calculated as follows $$\sigma^{t1} = \begin{cases} 5° \text{ C.,} & \text{initial value} \\ \sigma^{t1} + 0.1° \text{ C.,} & \text{IF } x^z_{t_{max}} \neq 0 \text{ or } x^g_{t_{max}} \neq 0, \\ \sigma^{t1} - 0.1° \text{ C.,} & \text{IF } x^z_{t_{max}} = 0 \text{ and } x^g_{t_{max}} = 0, \end{cases}$$

$\sigma^{t2}$ is the width of the bell-shaped function related to high temperatures and is calculated as follows:

$$\sigma^{t2} = \begin{cases} 20° \text{ C.,} & \text{initial value} \\ \sigma^{t2} + 0.1° \text{ C.,} & \text{IF } x^z_{t_{max}} \neq 0 \text{ or } x^g_{t_{max}} \neq 0, \\ \sigma^{t2} - 0.1° \text{ C.,} & \text{IF } x^z_{t_{max}} = 0 \text{ and } x^g_{t_{max}} = 0, \end{cases}$$

Consequently, the width and center of the bell change as a function of the cry intensity value at the time $t_{max}$. In particular, the initial value of $m^{t1}$ and of $m^{t2}$ are respectively 17.5° C. and 30° C., while the initial value of $\sigma^{t1}$ and $\sigma^{t2}$ are respectively 5° C. and 20° C. If at $$x^z_{t_{max}} \neq 0$$

(i.e., the cry intensity is different from zero) and/or $$x^g_{t_{max}} \neq 0$$

(i.e., the agitation intensity is different from 0), it means that the baby has not been soothed and therefore $m^{t1}$ and $m^{t2}$ are gradually increased by 0.1° C., while $\sigma^{t1}$ and $\sigma^{t2}$ are gradually increased by 0.05° C.; this is to contribute to a higher vibration intensity for the same mattress temperature. Vice versa, if at $t_{max}$ the cry intensity and the agitation intensity are equal to zero, it means that the baby has been soothed and therefore $m^{t1}$ and $m^{t2}$ are gradually decreased by 0.1° C., while $\sigma^{t1}$ and $\sigma^{t2}$ are gradually decreased by 0.05° C. to contribute to a lower vibration intensity at the same mattress temperature.

Preferably the membership function of $x^{tmin}$ is in accordance with the following formula:

$$\mu(x^{tmin}) = x^{tmin} * \gamma^{tmin}, \text{for } 0 \leq \gamma^{tmin} \leq 1$$

Where $\gamma^{tmin}$ is a dimensionless coefficient which follows the following trend:

$$\gamma^{tmin} = \begin{cases} 0.5, & \text{initial value} \\ \gamma^{tmin} + 0.05, & \text{IF } x^z_{t_{max}} \neq 0 \text{ or } x^g_{t_{max}} \neq 0, \\ \gamma^{tmin} - 0.05, & \text{IF } x^z_{t_{max}} = 0 \text{ and } x^g_{t_{max}} = 0, \end{cases}$$

Preferably the membership function of $x^{tmin}$ is in accordance with the following formula:

$$\mu(x^{tmax}) = x^{tmax} * \gamma^{tmax}, \text{ for } 0 \leq \gamma^{tmax} \leq 1$$

Where $\gamma^{tmax}$ is a dimensionless coefficient which follows the following trend:

$$\gamma^{tmax} = \begin{cases} 0.5, & \text{initial value} \\ \gamma^{tmax} + 0.05, & \text{IF } x^z_{t_{max}} \neq 0 \text{ or } x^g_{t_{max}} \neq 0, \\ \gamma^{tmax} - 0.05, & \text{IF } x^z_{t_{max}} = 0 \text{ and } x^g_{t_{max}} = 0, \end{cases}$$

The dimensionless coefficients $\gamma^{tmin}$ and $\gamma^{tmax}$ represent a weight and have a value between 0 and 1, associated with excessively low (i.e., below $T_{min}$) or excessively high temperatures (i.e., above $T_{max}$). The initial value of $\gamma^{tmin}$ and $\gamma^{tmax}$ (equal to 0.5) is increased or decreased by 0.05 depending on the value $$x^z_{t_{max}} \text{. and } x^g_{t_{max}}.$$

If they are different from zero and therefore the baby has not been soothed, the value of the dimensionless coefficient is increased by 0.05 and vice versa, decreased. This is to contribute to a higher (or lower in the opposite case) vibration intensity for the same mattress temperature.

Preferably another input of the controller 200 is the digital signal of the mattress humidity where the baby sleeps, which is deduced from the reading value of the humidity sensor H integrated in the mattress. The system digitally detects a humidity value, as a percentage. If the relative humidity value is higher than a reference threshold indicated as $H_{max}$ (e.g., 60%), the system detects such a condition as a confirmation that the mattress humidity is too high. The rule is as follows:

IF $x^h \geq H_{max}$ THEN THE MATTRESS HUMIDITY IS TOO HIGH and therefore $x^{hmax} = 1$ If the mattress humidity is too high, the membership function of the input $x^h$ is calculated, which is as follows:

$$\mu(x^h) = \exp\left(\frac{(x^h - m^h)^2}{(\sigma^h)^2}\right)$$

Where $m^h$ is the center of the bell-shaped function and is calculated as follows:

$$m^h = \begin{cases} 50\%, & \text{initial value} \\ m^h + 1\%, & \text{IF } x^z_{t_{max}} \neq 0 \text{ or } x^g_{t_{max}} \neq 0, \\ m^h - 1\%, & \text{IF } x^z_{t_{max}} = 0 \text{ and } x^g_{t_{max}} = 0, \end{cases}$$

$\sigma^h$ is the width of the bell-shaped function, and is calculated as follows:

$$\sigma^h = \begin{cases} 90\%, & \text{initial value} \\ \sigma^h + 1\%, & \text{IF } x^z_{t_{max}} \neq 0 \text{ or } x^g_{t_{max}} \neq 0, \\ \sigma^h - 1\%, & \text{IF } x^z_{t_{max}} = 0 \text{ and } x^g_{t_{max}} = 0, \end{cases}$$

Consequently, the width and center of the bell change as a function of the cry intensity value at the time $t_{max}$. In particular, the initial value of $m^h$ is 50% and the initial value of oh is 90%; if at $$x^z_{t_{max}} \neq 0$$

(i.e., the cry intensity is different from zero) and $$x^g_{t_{max}} \neq 0$$

(i.e., the agitation intensity is different from 0), it means that the baby has not been soothed and therefore $m^h$ and oh are gradually increased by 1% to contribute to a higher vibration intensity for the same frequency of the baby's cry. Vice versa, if at $t_{max}$, the cry intensity and the agitation intensity are equal to zero, it means that the baby has been soothed and therefore $m^h$ and $\sigma^h$ are gradually decreased by 1% to contribute to a lower vibration intensity for the same mattress humidity.

Preferably the membership function of $x^{h_{max}}$ is the following:

$$\mu(x^{h_{max}}) = x^{h_{max}} * \gamma^{h_{max}}, \text{ for } 0 \leq \gamma^{h_{max}} \leq 1$$

Where: $\gamma^{h_{max}}$ is the dimensionless coefficient applied to the condition "the mattress humidity is too high", which follows the following trend:

$$\gamma^{h_{max}} = \begin{cases} 0.5, \text{ initial value} \\ \gamma^{h_{max}} + 0.05, \text{ IF } x^z_{t_{max}} \neq 0 \text{ or } x^g_{t_{max}} \neq 0, \\ \gamma^{h_{max}} - 0.05, \text{ F } x^z_{t_{max}} = 0 \text{ and } x^g_{t_{max}} = 0, \end{cases}$$

The dimensionless coefficient $\gamma^{h_{max}}$ represents a weight and has a value between 0 and 1, associated with excessively high humidity (i.e., above $H_{max}$). The initial value of $\gamma^{h_{max}}$ (equal to 0.5) is increased or decreased by 0.05 as a function of the value at $t_{max}$ by $$x^z_{t_{max}}. \text{ and } x^g_{t_{max}}.$$

If at $t_{max}$, $$x^z_{t_{max}} \neq 0$$

(i.e., the cry intensity is different from zero) and $$x^g_{t_{max}} \neq 0$$

(i.e., the agitation intensity is different from 0), it means that the baby has not been soothed, the value of the dimensionless coefficient is increased by 0.05 and vice versa, decreased. This is to contribute to a higher (or lower in the opposite case) vibration intensity for the same mattress humidity.

Preferably another input of the controller 200 is the urination level $x^m$ of the baby's diaper and is deduced from the value of the digital mattress humidity signal $x^h$ and from the digital signal of the baby's weight $x^{pg}$. Two samples of these values measured at a given time t of 30 seconds are required to detect the urination level in the diaper. The rule is as follows:

$$IF \begin{cases} x^h_t > x^h_{t-1} \\ x^{pg}_t > x^{pg}_{t-1} \end{cases} \text{ THEN THE BABY IS WET and } x^m = 1$$

$$x^m = 0, \text{ otherwise}$$

If the baby is wet, the membership function of the input $x^m$ is calculated, "the baby is wet", which is the following:

$$\mu(x^m) = \begin{cases} x^m * \gamma^m, x^G = 0 \\ 0, x^G = 1 \end{cases}, \text{ for } 0 \leq \gamma^m \leq 1$$

Where: $x^G=1$ is the mother's indication that the diaper has been changed and $\gamma^m$ is the dimensionless coefficient applied to the condition "the baby is wet", which follows the following trend:

$$\gamma^m = \begin{cases} 0.5, \text{ initial value} \\ \gamma^m + 0.05, \text{ IF } x^z_{t_{max}} \neq 0 \text{ or } x^g_{t_{max}} \neq 0, \\ \gamma^m - 0.05, \text{ IF } x^z_{t_{max}} = 0 \text{ and } x^g_{t_{max}} = 0, \end{cases}$$

The dimensionless coefficient $\gamma^m$ represents a weight and has a value between 0 and 1, associated with the condition that the baby is wet. The initial value of $y^m$ (equal to 0.5) is increased or decreased by 0.05 as a function of the value at $t^{max}$, by $$x^z_{t_{max}}. \text{ and } x^g_{t_{max}}.$$

If at $t_{max}$, $$x^z_{t_{max}} \neq 0$$

i.e., the cry intensity is different from zero) and $$x^g_{t_{max}} \neq 0$$

(i.e., the agitation intensity is different from 0), it means that the baby has not been soothed, the value of the dimensionless coefficient is increased by 0.05 and vice versa, decreased. This is to contribute to a higher (or lower in the opposite case) vibration intensity for the same urination of the baby's diaper.

Preferably, the baby's parent can enter data on the baby's condition which can be considered as input variables which have a value of 0 or 1 respectively if they are not present or if they are present.

For example, the data that the baby has eaten can be considered as a variable $x^F$. which assumes the value 1 if the data that the baby has eaten has been entered, otherwise it assumes the value 0.

The membership function of the input x", "the baby has eaten".

$\mu(x^F)=\{1$, if the affirmation "the baby has eaten" is true 0, otherwise

Again, the fact that the baby has been changed can be considered as a variable $x^G$ which assumes the value 1 if the data that the baby has been changed has been entered, otherwise it assumes the value 0.

The membership function of the input x", "the baby has been changed".

$\mu(x^G)=\{1$, if the affirmation "the baby has been changed" is true 0, otherwise The data on the baby's weight can be considered as a variable $x^E$ which assumes the value 1 if the data on the baby's weight has been entered, otherwise it assumes the value 0.

The data that the baby is crying because the diaper is full can be considered as a variable $x^A$ which assumes the value 1 if the data that the baby is crying because the diaper is full has been entered, otherwise it assumes the value 0.

The membership function of the input $x^A$, "the baby's diaper is full".

$$\mu(x^A) = \begin{cases} 1, \text{ if the affirmation "the baby's diaper is full"} \\ \text{is true 0, otherwise} \end{cases}$$

The data that the baby is crying for another reason, for example for the reason B, can be considered as a variable $x^B$ which assumes the value 1 if the data that the baby is crying due to that reason has been entered, otherwise it assumes the value 0.

The membership function of the input $x^B$, "the baby is crying due to the reason B".

$$\mu(x^B) = \begin{cases} 1, \text{ if affirmation "the baby is crying due to reason B"} \\ \text{is true 0, otherwise} \end{cases}$$

Another input of the controller 200 is the digital signal related to the baby's weight $x^{pg}$ i.e., the baby's weight in grams. The value $s_g$ is measured for each force sensor F. This value is then multiplied by the sensor area $A_s$, $(s_g*A_s)$, for each sensor. The weight is then calculated by performing the following operation:

$$\frac{\sum_{j=1}^{i=a} \sum_{j=1}^{j=b} s_g(i;j)*A_s}{A_s * axb}$$

If the baby is moved, the weight is recalculated.
The rules are as follows:
IF $$X_{T+1}^{pg} > x_t^{pg}$$

THEN THE BABY HAS EATEN
where t is the sampling time (for example 30s).

If the baby's center of gravity has also changed, i.e.:

$$\begin{cases} S_{bar_{t+1}} = S_{bar_t} \\ x_{t+1}^{pg} > x_t^{pg} \end{cases} \text{THEN THE BABY'S DIAPER IS FULL}$$

The membership function of the input $x^{pg}$ is the following:

$$\mu(x^{pg}) = \begin{cases} \exp\left(\frac{(x^h - m^h)^2}{(\sigma^h)^2}\right), \text{ for } x^E = 0 \\ 0, \text{ for } x^E \neq 0, \end{cases}$$

Where $x^E$ is the weight indicated by the parent and $m^{pg}$ is the center of the bell-shaped function and is calculated as follows.

$$m^{pg} = \begin{cases} P \text{ initial value} \\ m^{pg} + 100 \text{ g, IF } x_{t_{max}}^z \neq 0 \text{ or } x_{t_{max}}^g \neq 0, \\ m^{pg} - 100 \text{ g, IF } x_{t_{max}}^z = 0 \text{ and } x_{t_{max}}^g = 0, \end{cases}$$

The parent manually confirms the baby's Gender and Age, so that the system assigns a value to P from the following table.

| P BY SEX MALE | AGE, IN MONTHS | P BY SEX FEMALE |
|---|---|---|
| 3.3 | 0 | 3.2 |
| 6 | 1-3 | 5.4 |
| 7.8 | 4-6 | 7.2 |
| 9.2 | 7-9 | 8.6 |
| 10.2 | 10-12 | 9.5 |
| 12.3 | 13-24 | 11.8 |
| 14.6 | 25-36 | 14.1 |

Until the mother manually enters the initial value P, this is equal to 8.9 Kg.

After deducting the value of P, the value of op is calculated by the system, the width of the bell-shaped function, calculated as follows:

$$\sigma^{pg} = \begin{cases} 2.000 \text{ g, initial value} \\ \sigma^{pg} + 0.05 \text{ g, IF } x_{t_{max}}^z \neq 0 \text{ or } x_{t_{max}}^g \neq 0, \\ \sigma^{pg} - 0.05 \text{ g, IF } x_{t_{max}}^z = 0 \text{ and } x_{t_{max}}^g = 0, \end{cases}$$

Consequently, the width and center of the bell change as a function of the cry intensity value at the time $t_{max}$. In particular, the initial value of $m^{pg}$ is defined by the table, while the initial value of $\sigma^{pg}$ is equal to 2 Kg. If at $t_{max}$, $$x_{t_{max}}^z \neq 0$$

(i.e., the cry intensity is different from zero) and $$x_{t_{max}}^g \neq 0$$

(i.e., the agitation intensity is different from 0), it means that the baby has not been soothed and therefore $m^{pg}$ is increased by 100 g, while $\sigma^{pg}$ is increased by 0.05 g; this is to contribute to a higher vibration intensity for the same weight of the baby. Vice versa, if at $t_{max}$, the cry intensity and the agitation intensity are equal to zero, it means that the baby has been soothed and therefore $m^{pg}$ is decreased by 100 g, while $\sigma^{pg}$ is decreased by 0.05 g to contribute to a lower vibration intensity for the same weight of the baby.

The apparatus 100 operates in accordance with the following method.

The control unit 1, in the presence of the baby's cry and/or agitation, controls the mattress vibration means PVM in a position P different from the baby's center of gravity on the mattress and within and not beyond a maximum time period $t_{max}$; this is to prevent the vibration from occurring in the portions of the mattress where the baby's sensitive parts are found, such as the head.

Preferably, the control unit 1 controls the vibration of only one or more actuators PVM which are in a different position than the position of the baby's center of gravity.

Preferably, once the input signals have been received and the various values of the digital variables or signals x have been calculated, the functions $\mu(x)$ are weighted and the vibration of the mattress is determined as a function of the weighting thereof.

In particular, the output signal from the controller 200 is the y signal given by y=Vibr×Ti where Vibr is the vibration intensity of the motor PVM and Ti is the duration of the vibration which varies over time following a function Ti(t) described below and with a maximum duration equal to $t_{max}$. The y signal is output only if the analog signal on the cry intensity $x^z$ is different from zero and/or the digital signal related to agitation $x^g$ is different from zero.

The vibration is performed in the position P which is different from the baby's center of gravity on the mattress; preferably the position P, if the center of gravity does not coincide with the center thereof, is a position complementary to the baby's center of gravity with respect to the mattress length and width, i.e., considering the position of the center of gravity $s_{bar}$ of the baby given by the Cartesian coordinates $c_{bar}$, $y_{bar}$, the position P is given by the difference between $x_{max}$, which is the dimension in cm of the mattress along the axis x, and $x_{bar}$ and $y_{max}$, which is the size in cm of the mattress along the y axis, and $y_{bar}$:

$$P = \{x_{max} - x_{bar}; y_{max} - y_{max}\}$$

If the center of gravity coincides with the center of the mattress, a position around the center of the mattress is chosen as position P.

The vibration intensity Vibr can assume values between O and 1 and is calculated as follows:

$$Vibr = 1 - \frac{\left(\sum_{\text{max}} - \sum\right)}{\sum_{\text{max}}}$$

Where $\Sigma$ is the sum of the membership functions $\mu(x)$ related to said inputs, i.e., the sum of the values of the membership functions $\mu(x^{pg})$, $\mu(x^z)$, $\mu(x^a)$, $\mu(x^g)$, $\mu(x^r)$, $\mu(x^h)$, $\mu(x^m)$, $\mu(x^f)$, $\mu(x^B)$, $\mu(x^G)$, $\mu(x^A)$, or only some of them if not all the inputs are present but only some and Emax is the value of the summation in which the membership functions are at the maximum value.

Once the value of Vibr has been obtained, it is approximated to the upper threshold, to place it within one of the ten brackets of the table below where, on the left, there is the approximate value of the brackets of the vibration intensity Vibr (indicated as Vibr scale) and, on the right, the current Ivibr in milliamps (mA) applied to the vibration means or actuators PVM which are in the position P, for each single reference bracket. The vibration of the mattress is activated only if the digital signal on the cry intensity $x^z$ is different from zero and/or the digital signal related to the agitation $x^g$ is different from zero.

| Vibr scale | Ivibr (mA) |
|---|---|
| 0.00 | 0 |
| 0.01 ÷ 0.10 | 26 |
| 0.11 ÷ 0.20 | 28 |
| 0.21 ÷ 0.30 | 30 |
| 0.31 ÷ 0.40 | 33 |
| 0.41 ÷ 0.50 | 35 |
| 0.51 ÷ 0.60 | 37 |
| 0.61 ÷ 0.70 | 39 |
| 0.71 ÷ 0.80 | 43 |
| 0.81 ÷ 0.00 | 46 |
| 0.91 ÷ 1.00 | 49 |

Ti varies over time, considering a maximum duration equal to $t_{max}$, thereby:

$$Ti(t) = \begin{cases} 1, \text{ for } t < t_{min} \\ 1 - \frac{2}{\beta^2} * (t - t_{min})^2, \text{ for } t_{min} < t < t_{min} + \frac{\beta}{2}. \\ \frac{2}{\beta^2} * (t - t_{min} + \beta)^2, \text{ for } t_{min} + \frac{\beta}{2} < t < t_{min} + \beta. \\ 0, \text{ for } t > t_{min} + \beta. \end{cases}$$

Where:
the parameter $\beta$ is calculated as follows:

$$\beta = \begin{cases} 5 \text{ minutes, as starting value} \\ \beta + 1 \text{ minute, } x^z_{t_{max}} \neq 0 \text{ or } x^g_{t_{max}} \neq 0, \\ \beta - 1 \text{ minute, } x^z_{t_{max}} = 0 \text{ and } x^g_{t_{max}} = 0, \\ 1 \text{ minute} \leq \beta \leq 10 \text{ minutes} \end{cases}$$

the parameter $t_{max}$ is calculated as follows:

$$T_{min} = \begin{cases} 1 \text{ minute, as starting value} \\ t_{min} + 1 \text{ minute, } x^z_{t_{max}} \neq 0 \text{ or } x^g_{t_{max}} \neq 0, \\ t_{min} - 1 \text{ minute, } x^z_{t_{max}} = 0 \text{ and } x^g_{t_{max}} = 0, \\ \text{with } t_{min} > 1 \text{ minute} \end{cases}$$

and where $$x^z_{t_{max}} \cdot \text{ and } x^g_{t_{max}}.$$

are respectively the values of the cry intensity and of the agitation intensity at the time $t_{max}$ of the previous operation carried out by the apparatus 100 when the baby has cried or is agitated and after the vibration of the mattress has occurred for the time period from 0 to $t_{max}$. If within the time $t_{max}$ the set vibration is capable of soothing the baby, the values Vibr, the time period Tvibr required for soothing the baby and the function $\mu(x)$ of greater weight which determined the baby's soothing are recorded in the memory SD of the control unit 1 so that the apparatus 100 can self-learn that when the same conditions occur, i.e., with the same function $\mu(x)$ of greater weight, the baby can be soothed with the same vibration value. Furthermore, the baby soothing system in accordance with the present invention is a closed-loop system since the presence or absence of the baby's cry and/or agitation upon reaching the time $t_{max}$ is a value which is taken up in the determination of the various functions $\mu(x)$ described above and is indicated $$x^z_{t_{max}},$$

and $$x^g_{t_{max}}.$$

If after the time $t_{max}$ the baby continues to cry, a message is sent to a parent and the function $\mu(x)$ of greater weight which was used in the vibration intensity value Vibr is recorded to characterize the baby's cry.

What is claimed is:

1. An apparatus for soothing a baby on a mattress, said apparatus comprising a mattress support or base including:

a plurality of force sensors configured to detect forces exerted by the baby on the mattress, a plurality of microphones configured to detect a cry of the baby, and piezoelectric actuators for vibrating the mattress, the apparatus further comprising a control unit configured to determine a center of gravity of the baby on the mattress and an agitation of the baby based on signals from said plurality of force sensors, wherein said control unit is configured to control said piezoelectric actuators to vibrate the mattress in a position different from the center of gravity of the baby on the mattress within and not beyond a maximum time period in response to detection of at least one of the cry of the baby or the agitation of the baby.

2. The apparatus of claim 1, wherein said plurality of force sensors are arranged according to a matrix scheme and at a certain distance from one another on said mattress support or base, and wherein said control unit is configured to calculate the center of gravity of the baby on the mattress from data detected by said plurality of force sensors.

3. The apparatus of claim 2, wherein said control unit is configured to determine the agitation of the baby by verifying a variation of forces detected by at least one force sensor of said plurality of force sensors in two successive time instants.

4. The apparatus of claim 3, wherein said control unit includes an executive software and a memory in which said executive software is installed, said executive software operating according to a fuzzy logic wherein base rules are defined and membership functions relating to at least a first input signal and a second input signal are processed, wherein the first input signal is a signal of each force sensor and said second input signal is an audio signal relating to the cry of the baby, wherein said control unit is configured to determine a membership function relating to the of the baby agitation and a membership function relating to the cry of the baby, and wherein an intensity of the vibration of the mattress is determined as a function of weighting of the membership functions relative to at least one of the agitation of the baby or the cry of the baby.

5. The apparatus of claim 4, wherein said control unit is configured to receive a third input signal relating to an intensity of the cry of the baby and a fourth input signal relating to a humidity level of the mattress, wherein said control unit is configured to determine membership functions relative to the third input signal and the fourth input signal if the baby cries and the humidity level of the mattress is higher than a threshold value, wherein the intensity of the vibration of the mattress is determined as a function of the weighting of the membership functions relative to the agitation of the baby, the cry of the baby, the intensity of the cry of the baby, and the humidity level of the mattress.

6. The apparatus of claim 5, further comprising a temperature sensor configured to detect a temperature of the mattress, wherein said control unit receives a fifth input signal relating to said temperature of the mattress, wherein said control unit is configured to determine the weight of the baby based on signals from said plurality of force sensors, and wherein said control unit is configured to determine the membership functions relating to said weight of the baby, said temperature of the mattress, and a urination level of a diaper of the baby if respectively a mattress temperature value is under a minimum value or over a maximum value and the baby got wet, wherein the intensity of the vibration of the mattress is determined as a function of the weighting of the membership functions relative to the agitation of the baby, the cry of the baby, the intensity of the cry of the baby, the humidity level of the mattress, the weight of the baby, the temperature of the mattress, and the urination level of the diaper of the baby.

7. The apparatus of claim 6, wherein said control unit is configured to receive data input by a user regarding a condition of the baby, said data being stored in said memory, wherein said control unit is configured to determine membership functions relating to said data, each membership function assuming a respective value according to a presence or absence of said data, and wherein the intensity of the vibration of the mattress is determined as a function of the weighting of the membership functions relative to the agitation of the baby, the cry of the baby, the intensity of the cry of the baby, the humidity level of the mattress, the weight of the baby, the temperature of the mattress, the urination level of the diaper of the baby, and said data.

8. The apparatus of claim 7, wherein said control unit is configured to adjust the membership functions relating to the agitation of the baby, the cry of the baby, the intensity of the cry of the baby, the humidity level of the mattress, the weight of the baby, and the temperature of the mattress based on the presence or absence of the cry of the baby and/or the agitation of the baby during a maximum time period relating to a preceding operation executed by said apparatus.

9. The apparatus of claim 6, wherein said control unit is configured to adjust a maximum time period relating to a preceding operation executed by said apparatus based on a presence or absence of the cry of the baby and/or the agitation of the baby during the maximum time period.

10. The apparatus of claim 1, further comprising a capacitor supplied with an electric signal generated by said plurality of microphones, wherein said control unit is configured to determine an intensity of the cry of the baby corresponding to a voltage across said capacitor.

11. The apparatus of claim 1, further comprising a humidity sensor configured to detect a humidity level of the mattress, wherein said control unit is configured to detect a urination level of a diaper of the baby as a function of a variation said humidity level and a variation of forces detected by said plurality of force sensors in two successive time instants.

12. The apparatus of claim 1, wherein said control unit is configured to detect if the baby filled a diaper as a function of a variation of the center of gravity of the baby on the mattress and a variation of the forces detected by said plurality of force sensors in two successive time instants.

\* \* \* \* \*